United States Patent
Jung et al.

(10) Patent No.: US 6,372,935 B1
(45) Date of Patent: Apr. 16, 2002

(54) COPOLYMER RESIN, PREPARATION THEREOF, AND PHOTORESIST USING THE SAME

(75) Inventors: Min Ho Jung; Jae Chang Jung; Cheol Kyu Bok; Ki Ho Baik, all of Kyoungki-do (KR)

(73) Assignee: Hyundai Electronics Industries Co., Ltd., Kyoungki (KR)

( * ) Notice: Subject to any disclaimer, the term of this patent is extended or adjusted under 35 U.S.C. 154(b) by 0 days.

(21) Appl. No.: 09/861,394

(22) Filed: May 18, 2001

Related U.S. Application Data

(62) Division of application No. 09/208,650, filed on Dec. 10, 1998, now Pat. No. 6,248,847.

(30) Foreign Application Priority Data

Dec. 31, 1997 (KR) ............................................ 97/81370

(51) Int. Cl.[7] .............................................. C07C 69/74
(52) U.S. Cl. ...................... 560/126; 560/118; 560/224; 526/262; 526/282
(58) Field of Search ................................ 560/224, 126, 560/118; 526/262, 282

(56) References Cited

U.S. PATENT DOCUMENTS 4,986,648 A  *  1/1991  Kobayashi et al.
5,621,019 A  *  4/1997  Nakano et al.

* cited by examiner

*Primary Examiner*—Paul J. Killos
*Assistant Examiner*—Hector M Reyes
(74) *Attorney, Agent, or Firm*—Marshall, Gerstein, & Borun.

(57) ABSTRACT

The present invention relates to a copolymer resin for ultra-shortwave light source such as KrF or ArF, process for preparation thereof, and photoresist comprising the same resin. The copolymer resin according to the present invention is easily prepared by conventional radical polymerization due to the introduction of norbornyl(meth)acrylate unit to a structure of copolymer for photoresist. The resin has high transparency at 193 nm wavelength, provides increased etching resistance and enhanced adhesive strength due to a hydrophilic functional group in the norbornyl group, and shows excellent resolution of 0.15 Fm in practical experiment of patterning.

14 Claims, No Drawings

COPOLYMER RESIN, PREPARATION THEREOF, AND PHOTORESIST USING THE SAME

This is a divisional application of U.S. application Ser. No. 09/208,650, filed Dec. 10, 1998, now U.S. Pat. No. 6,248,847.

BACKGROUND OF THE INVENTION

The present invention relates generally to a technique including a process and resulting structure for a copolymer resin for an ultra-shortwave light source such as KrF or ArF. More specifically, it relates to a copolymer resin, where a norbornyl(meth)acrylate unit is introduced to a copolymeric structure for a photo resist. The photo resist can be used in a variety of lithography processes using a KrF (248 nm) or ArF (193) light source which is a light source to be applied in next generation memory elements such as 1 G or 4 G DRAM integrated circuit chips.

In general, characteristics such as etching resistance, adhesiveness with low light absorption at 193 nm wavelength are often desired for a copolymer resin for ArF. The copolymer resin should also be developable by using, for example, a 2.38 wt % aqueous solution of tetramethylammonium hydroxide (TMAH). It is difficult, however, to synthesize a copolymer resin satisfying some or all these desirable characteristics. Many researches have often focused on studies on a norbolac type resin as a material to increase transparency at 193 nm wavelength and increase etching resistance. Thus, attempts to employ(meth)acrylate resins having high transparency, and to introduce alicyclic compounds to resin side chains in order to overcome limitations of deficient etching resistance, have been suggested. For example, IBM suggested the use of a copolymer resin represented by following chemical formula I:

[FORMULA I]

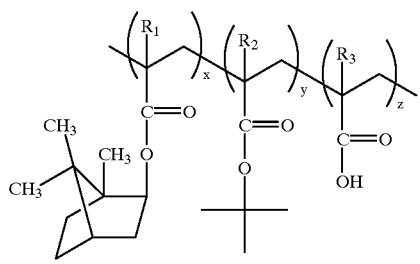

where $R_1$, $R_2$ and $R_3$ independently represent hydrogen or methyl.

The copolymer resin represented by chemical formula I unfortunately has increased hydrophobicity. The increased hydrophobicity occurs, in part, from introducing an alicyclic compound to the side chain, which decreases solubility in the developing solution and weakens adhesiveness, so that the compound can be contained in the copolymer resin composition in an amount not more than a certain level. It should be noted that if the alicyclic compound is included at less than the certain level, satisfactory etching resistance cannot generally be achieved. It has been found that, among the conventional alicyclic groups on side chains, which are commonly known, the norbornyl or admantyl group is effective in view of etching resistance. The conventional copolymer resin including formula I has a severe limitation in that adhesive strength decreases by gaining hydrophobicity as the content of the cyclic compound in the resin composition increases.

From the above, it is seen that an improved photo resist that has improved characteristics is highly desirable.

SUMMARY OF THE INVENTION

The present inventors have performed intensive studies to overcome the above problems encountered in conventional photo resist products, and as a result, they found a copolymer resin composition having high transparency at 193 nm wavelength and high etching resistance.

In a specific embodiment, the present copolymer resin is prepared by radical polymerization techniques. These techniques include a variety of steps such as introducing norbornyl(meth)acrylate unit in a copolymer resin for photo resist. An adhesive strength of the resin can be increased by introducing a hydrophilic group in norbornyl group. A significant difference of solubility to the developing solution between the exposed region and non-exposed region can be provided through the processes of introducing a suitable protecting group, exposing, and deprotecting by post-heating step.

In an alternative embodiment, the present invention provides a monomer comprising a 5-hydroxy-6-norbornyl (meth)acrylate derivative. In a further embodiment, the present invention provides a process for preparing the monomer. In still a further embodiment, the present invention provides a copolymer resin comprising 5-hydroxy-6-norbornyl(meth)acrylate derivative and a process for preparing the copolymer resin. Among other aspects, the invention also provides photo resist comprising the copolymer resin or resins. Still further, the present invention provides a process for manufacturing the photo resist and a semiconductor element having a pattern formed by using the photo resist. These and other embodiments will be described throughout the present specification and more particularly below.

The present invention achieves these benefits in the context of known process technology. However, a further understanding of the nature and advantages of the present invention may be realized by reference to the latter portions of the specification and attached drawings.

DETAILED DESCRIPTION OF THE INVENTION

In a specific embodiment, the present invention relates generally to a copolymer resin comprising 5-hydroxy-6-norbornyl(meth)acrylate derivative represented by chemical formula II:

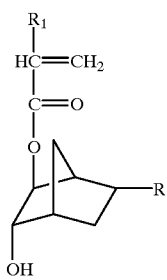

where R represents 2-tert-butoxycarbonyl, 2-carboxylic, 2-hydropyranyloxycarbonyl, 2-hydroxyfuranyloxycarbonyl or 2-ethoxyethyloxycarbonyl; $R_1$ represents hydrogen or methyl.

The copolymer resin according to the present invention preferably includes copolymers represented by chemical formula III to VII.

(1) Poly[2-tert-butoxycarbonyl-5-hydroxy-6-norbornyl (meth)acrylate/2-carboxylic-5-hydroxy-6-norbornyl(meth) acrylate] copolymer resin (Molecular Weight: 4,000 to 100,000)

[FORMULA III]

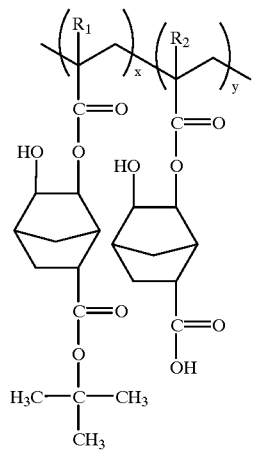

[In the formula, $R_1$ and $R_2$ independently represent hydrogen or methyl, and x and y independently represent a mole fraction between 0.001 and 0.99.]

(2) Poly[2-tert-butoxycarbonyl-5-hydroxy-6-norbornyl (meth)acrylate/2-hydroxyethyl(meth)acrylic acid/(meth) acrylic acid] copolymer resin (Molecular Weight: 4,000 to 100,000)

[FORMULA IV]

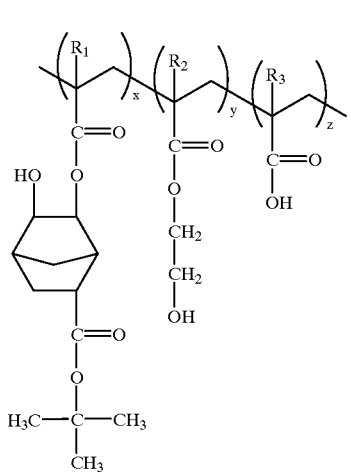

[In the formula, $R_1$, $R_2$ and $R_3$ independently represent hydrogen or methyl, and x, y and z independently represent a molar fraction between 0.001 and 0.99.]

(3) Poly[2-hydroxypyranyloxycarbonyl-5-hydroxy-6-norbornyl(meth)acrylate/2-hydroxyethyl(meth)acrylate/ (meth)acrylic acid] copolymer resin (Molecular Weight: 4,000 to 100,000)

[FORMULA V]

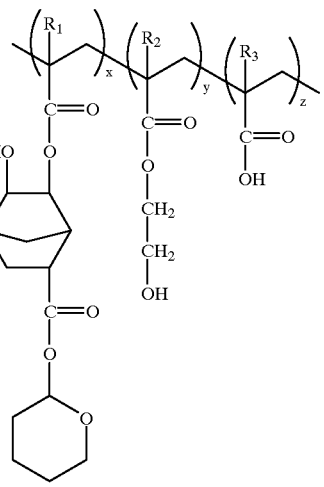

[In the formula, $R_1$, $R_2$ and $R_3$ independently represent hydrogen or methyl, and x, y and z independently represent a mole fraction between 0.001 and 0.99.]

(4) Poly[2-hydrofuranyloxycarbonyl-5-hydroxy-6-norbornyl(meth)acrylate/2-hydroxyethyl(meth)acrylate/ (meth)acrylic acid] copolymer resin (Molecular Weight: 4,000 to 100,000)

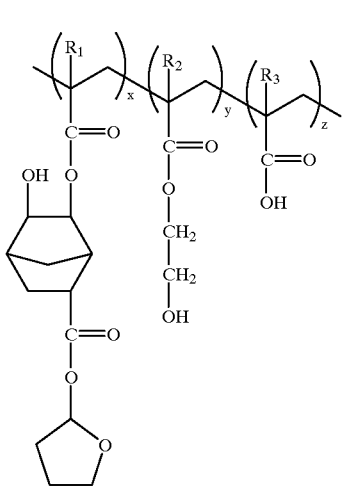

[FORMULA VI]

[In the formula, $R_1$, $R_2$ and $R_3$ independently represent hydrogen or methyl, and x, y and z independently represent a mole fraction between 0.001 and 0.99.]

(5) Poly[2-ethoxyethyloxycarbonyl-5-hydroxy-6-norbornyl (meth)acrylate/2-hydroxyethyl(meth)acrylate/(meth)acrylic acid] copolymer resin (Molecular Weight: 4,000 to 100,000)

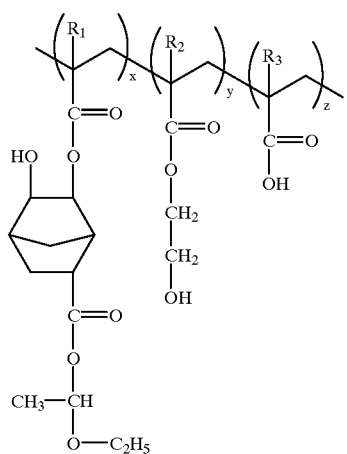

[FORMULA VII]

[In the formula, $R_1$, $R_2$ and $R_3$ independently represent hydrogen or methyl, and x, y and z independently represent a mole fraction between 0.001 and 0.99.]

The copolymer resin of formula III according to the present invention can be prepared by reacting 2-tert-butoxycarbonyl-5-hydroxy6norbornyl(meth)acrylate with 2-carboxylic-5-hydroxy-6-norbornyl(meth)acrylate in the presence of a conventional polymerization initiator, as illustrated in reaction scheme I:

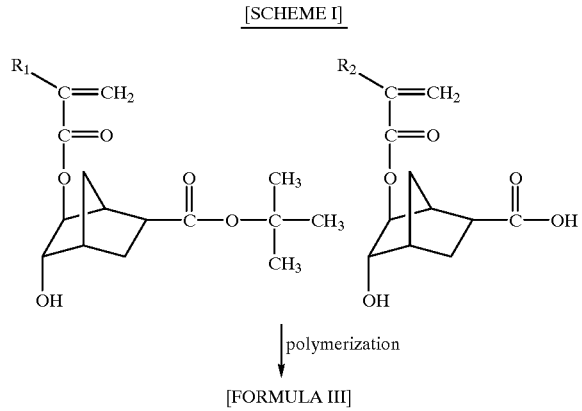

[SCHEME I]

polymerization

[FORMULA III]

where $R_1$ and $R_2$ independently represent hydrogen or methyl.

The copolymer resin of formula IV according to the present invention can be prepared by reacting 2-tert-butoxycarbonyl-5-hydroxy-6-norbornyl(meth)acrylate with 2-hydroxyethyl(meth)acrylate in the presence of a conventional polymerization initiator, as illustrated in reaction scheme II:

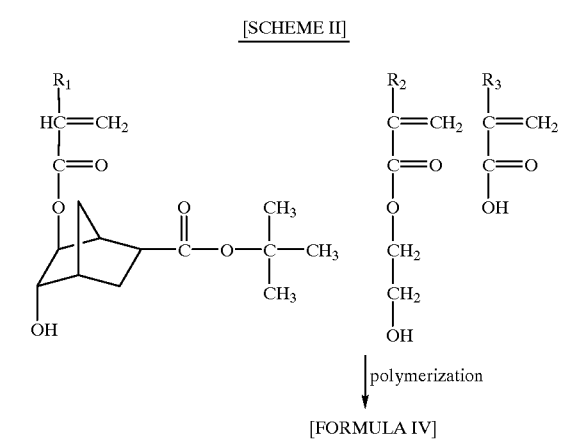

[SCHEME II]

polymerization

[FORMULA IV]

where $R_1$, $R_2$ and $R_3$ independently represent hydrogen or methyl.

The copolymer resin of formula V according to the present invention can be prepared by reacting 2-hydroxypyranyloxycarbonyl-5-hydroxy-6-norbornyl (meth)acrylate, 2-hydroxyethyl(meth)acrylate and (meth) acrylic acid in the presence of a conventional polymerization initiator, as illustrated in reaction scheme III:

[SCHEME III]

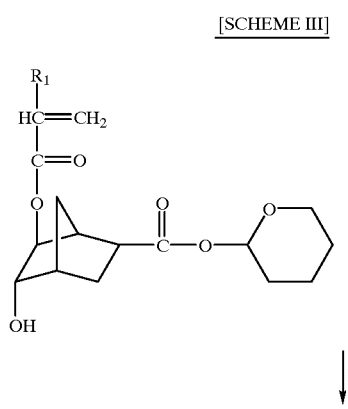

↓ polymerization

[FORMULA V]

wherein, $R_1$, $R_2$ and $R_3$ independently represent hydrogen or methyl.

The copolymer resin of formula VI according to the present invention can be prepared by reacting 2-hydrofuranyloxycarbonyl-5-hydroxy-6-norbornyl(meth)acrylate, 2-hydroxyethyl(meth)acrylate and (meth)acrylic acid in the presence of a conventional polymerization initiator, as illustrated in reaction scheme IV:

[SCHEME IV]

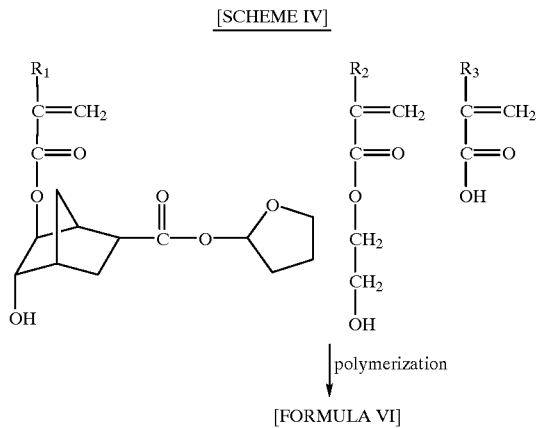

↓ polymerization

[FORMULA VI]

where $R_1$, $R_2$ and $R_3$ independently represent hydrogen or methyl.

The copolymer resin of formula VII according to the present invention can be prepared by reacting 2-ethoxyethyloxycarbonyl-5-hydroxy-6-norbornyl(meth)acrylate, 2-hydroxyethyl(meth)acrylate and (meth)acrylic acid in the presence of a conventional polymerization initiator, as illustrated in reaction scheme V:

[SCHEME V]

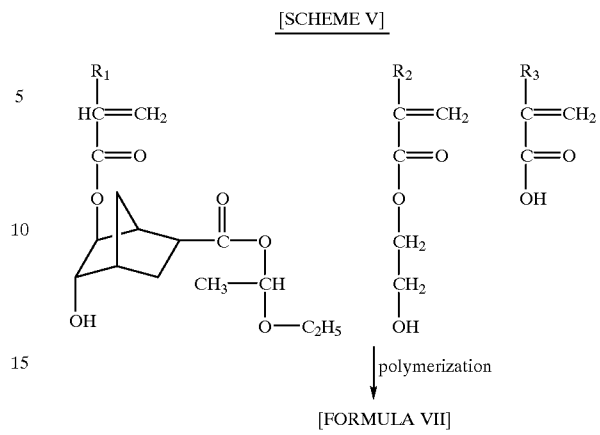

↓ polymerization

[FORMULA VII]

wherein $R_1$, $R_2$ and $R_3$ independently represent hydrogen or methyl.

The copolymer resins (formula III to VII) according to the present invention can be prepared by a conventional polymerization process such as bulk polymerization or solution polymerization. Polymerization initiators usable in the present invention include benzoyl peroxide, 2,2'-azobisisobutyronitrile (AIBN), acetyl peroxide, lauryl peroxide, tert-butyl peracetate, di-tert-butyl peroxide, or the like. As a reaction solvent, cyclohexanone, methyl ethyl ketone, benzene, toluene, dioxane and/or dimethylformamide may be used individually, or in a mixture.

In the process for preparing the copolymer resin according to the present invention, general polymerization condition including temperature and pressure of radical polymerization may be controlled dependent upon the property of the reactants, but it is preferable to carry out the polymerization reaction at a temperature between 60 and 200 EC under nitrogen or argon atmosphere for 4 to 24 hours.

The copolymer resin according to the present invention can be used as a chemical amplification photoresist, which is prepared by polymerizing (meth)acrylate derivatives in which norbornyl group having a hydrophilic group has been introduced to the side chain. The photoresist has high glass transition temperature which is required in the course of the manufacturing process, and has rare absorption at 193 Fm, and the protective group therein can be easily removed. In addition, the norbornyl group synthesized to have hydrophilicity increases adhesiveness. The copolymer resin prepared according to the present invention can be advantageously used in lithography process, which is expected to be applied in 1 G or 4 G DRAM.

The copolymer resin of the present invention can be prepared according to a conventional process of photoresist composition, that is, by mixing conventional inorganic acid generator in the presence of organic solvent to manufacture photoresist solution. The photoresist can be used in the formation of positive micro-image. In the process for forming photoresist pattern of semiconductor element, the amount of the copolymer resin according to the present invention depends on the organic solvent or inorganic acid generator used, and the condition of lithography, but conventionally it is about 10 to 30% by weight on the basis of the organic solvent used in the preparation of the photoresist.

The process for forming a photoresist pattern of a semiconductor element by using the copolymer resin according to the present invention is described in detail here-in-below:

The copolymer resin according to the present invention is dissolved in cyclohexanone at a concentration of 10 to 30% by weight. Sulfonium salt or organic sulfonic acid (0.1 to 10% by weight of copolymer resin), as an inorganic acid generator, is added to the copolymer resin solution. The mixture was then filtered with ultra-micro filter to prepare photoresist solution. The inorganic acid generators which can be used in the process include triphenylsulfonium triplate, dibutylnaphthylsulfonium triplate, 2,6-dimethylphenylsulfonate, bis(arylsulfonyl)-diazomethane, oxime sulfonate, 2,1-diazonaphthoquinon-4-sulfonate, or the like. The photoresist solution is spin-coated on a silicon wafer to prepare a thin film, which is then preheated in an oven or on a heating plate at 80–150 EC for 1–5 minutes, exposed to light by using far ultraviolet exposer or an eximer laser exposer, and post-heated at a temperature between 100 EC and 200 EC for 1 second to 5 minutes. The exposed wafer is impregnated in 2.38% aqueous TMAH solution for 1 to 1.5 minutes to obtain a positive photoresist pattern.

A better understanding of the present invention may be obtained in light of following examples which are set forth to illustrate, but are not to be construed to limit, the present invention.

Preparation Example I

Synthesis of 2-tert-butoxycarbonyl-5-hydroxy-6-norbornyl(meth)acrylate

Via Diels-Alder reaction of cyclopentadiene with tert-butylacrylate, 2-tert-butoxycarbonyl-5-norbornene was synthesized.

Twenty five grams (25 g) of, 2-tert-butoxycarbonyl-5-norbornene thus prepared was added to acetone (150 ml). After well mixing, the mixture was chilled to −60 EC. Potassium permanganate ($KMnO_4$) (8.15 g) was added in small portions to the solution, and the reaction was performed at −60 EC for 1 hour.

Then aqueous alkaline solution was slowly added, and the temperature was slowly raised to reach room temperature. At the same temperature, the reaction was proceeded for 1.5 hours. From the reaction mixture, manganese dioxide was filtered off, and the mixture was washed several times with acetone, and then concentrated by using a rotary evaporator under reduced pressure.

The reaction mixture was extracted with dichloromethane, and the extract was evaporated under reduced pressure. The residue was purified by silica gel column chromatography to give 22.7 g (yield: 80%) of 2-t-butoxycarbonylnorbornan-5,6-diol.

In a 500 ml round-bottomed flask, tetrahydrofuran (100 ml) was charged, and 2-tert-butoxycarbonylnorbornan-5,6-diol (10 g) and triethylamine (13.4 g) were dissolved therein. (Meth)acryloyl chloride (4.6 g) was slowly added, and the resultant mixture was reacted at −10 EC for 6 hours. The reaction mixture was filtered, and evaporated under reduced pressure. The residue was purified by column chromatography to give 9.4 g (yield: 72%) of 2-tert-butoxycarbonyl-5-hydroxy-6-norbornyl(meth)acrylate.

Preparation Example II

Synthesis of 2-carboxylic-5-hydroxy-6-norbornyl(meth)acrylate

Via Diels-Alder reaction of cyclopentadiene with acrylic acid, 5-norbornene carboxylic acid was synthesized.

Twenty grams (20 g) of 5-norbornene carboxylic acid thus prepared was added to acetone (150 ml). After well mixing, the mixture was chilled to −60 EC.

Potassium permanganate ($Kmno_4$) (8.15 g) was added in small portions to the solution, and the reaction was performed at −60 EC for 1 hour. Then aqueous alkaline solution was slowly added, and the temperature was slowly raised to reach room temperature. At the same temperature, the reaction was proceeded for 1.5 hours. After filtering off manganese dioxide, the reaction mixture was washed several times with acetone, and then concentrated by using a rotary evaporator under reduced pressure. The reaction mixture was extracted with dichloromethane, and the extract was evaporated under reduced pressure. The residue was purified by silica gel column chromatography to give 14.7 g (yield: 73%) of 5-norbornene carboxylic-5,6-diol.

In a 500 ml round-bottomed flask, tetrahydrofuran (100 ml) was charged, and 5-norbornene carboxylic-5,6-diol (8 g) and triethylamine (11.4 g). were dissolved therein. (Meth)acryloyl chloride (3.5 g) was slowly added, and the resultant mixture was reacted at −10 EC for 6 hours. The reaction mixture was filtered, and evaporated under reduced pressure. The residue was purified by column chromatography to give 8.3 g (yield: 70%) of 2-carboxylic-5-hydroxy-6-norbornyl (meth)acrylate.

Preparation Example III

Synthesis of 2-hydropyranyloxycarbonyl-5-hydroxy-6-norbornyl(meth)acrylate

Via Diels-Alder reaction of cyclopentadiene with hydropyranyl acrylate, 2-hydropyranyloxycarbonyl-5-norbornene was synthesized.

Twenty two grams (22 g) of 2-pyranyloxycarbonyl-5-norbornene thus prepared was added to acetone (150 ml). After well mixing, the mixture was chilled to −60 EC. Potassium permanganate ($KMnO_4$) (7.45 g) was added in small portions to the solution, and the reaction was performed at −60 EC for 1 hour. Then aqueous alkaline solution was slowly added, and the temperature was slowly raised to reach room temperature. At the same temperature, the reaction was proceeded for 1.5 hours. After filtering off manganese dioxide, the reaction mixture was washed several times with acetone, and then concentrated by using a rotary evaporator under reduced pressure. The reaction mixture was extracted with dichloromethane, and the extract was evaporated under reduced pressure. The residue was purified by silica gel column chromatography to give 20.6 g (yield:77%) of 2-hydropyranyloxycarbonylnorbornan-5,6-diol.

In a 500 ml round-bottomed flask, tetrahydrofuran (100 ml) was charged, and 2-hydropyranyloxycarbonylnorbornan-5,6-diol (9 g) and triethylamine (12.1 g) were dissolved therein. (Meth)acryloyl chloride (4.8 g) was slowly added, and the resultant mixture was reacted at −10 EC for 6 hours. The reaction mixture was filtered, and evaporated under reduced pressure. The residue was purified by column chromatography to give 9.8 g (yield: 76%) of 2-hydropyranyloxycarbonyl-5-hydroxy-6-norbornyl(meth)acrylate.

Preparation Example IV

Synthesis of 2-hydrofuranyloxycarbonyl-5-hydroxy-6-norbornyl(meth)acrylate

Via Diels-Alder reaction of cyclopentadiene with hydrofuranyl acrylate, 2-hydrofuranyloxycarbonyl-5-norbornene was synthesized.

Twenty one grams (21 g) of 2-hydrofuranyloxycarbonyl-5-norbornene thus prepared was added to acetone (150 ml). After well mixing, the mixture was chilled to −60 EC. Potassium permanganate ($KmnO_4$) (7.40 g) was added in small portions to the solution, and the reaction was performed at −60 EC for 1 hour. Then aqueous alkaline solution was slowly added, and the temperature was slowly raised to reach room temperature. At the same temperature, the reaction was proceeded for 1.5 hours. After filtering off manganese dioxide, the reaction mixture was washed several times with acetone, and then concentrated by using a rotary evaporator under reduced pressure. The reaction mixture was extracted with dichloromethane, and the extract was evaporated under reduced pressure. The residue was purified by silica gel column chromatography to give 20.1 g (yield: 76%) of 2-hydrofuranyloxycarbonylnorbornan-5,6-diol.

In a 500 ml round-bottomed flask, tetrahydrofuran (100 ml) was charged, and 2-hydrofuranyloxycarbonylnorbornan-5,6-diol (8.8 g) and triethylamine (11.1 g) were dissolved therein. (Meth)acryloyl chloride (4.6 g) was slowly added, and the resultant mixture was reacted at −10 EC for 6 hours. The reaction mixture was filtered, and evaporated under reduced pressure. The residue was purified by column chromatography to give 9.4 g (yield: 75%) of 2-hydrofuranyloxycarbonyl-5-hydroxy-6-norbornyl(meth)acrylate.

Prepartion Example V

Synthesis of 2-ethoxyethyloxycarbonyl-5-hydroxy-6-norbornyl(meth)acrylate

Via Diels-Alder reaction of cyclopentadiene with ethoxyethyl acrylate, 2-ethoxyethyloxycarbonyl-5-norbornene was synthesized.

Twenty grams (20 g) of 2-ethoxyethyloxycarbonyl-5-norbornene thus prepared was added to acetone (150 ml). After well mixing, the mixture was chilled to −60 EC. Potassium permanganate ($KMnO_4$) (7.12 g) was added in small portions to the solution, and the reaction was performed at −60 EC for 1 hour. Then aqueous alkaline solution was slowly added, and the temperature was slowly raised to reach room temperature. At the same temperature the reaction was proceeded for 1.5 hours. After filtering off manganese dioxide, the reaction mixture was washed several times with acetone, and then concentrated by using a rotary evaporator under reduced pressure. The reaction mixture was extracted with dichloromethane, and the extract was evaporated under reduced pressure. The residue was purified by silica gel column chromatography to give 18.1 g (yield: 74%) of 2-ethoxyethyloxycarbonylnorbornan-5,6-diol.

In a 500 ml round-bottomed flask, tetrahydrofuran (100 ml) was charged, and 2-ethoxyethyloxycarbonylnorbornan-5,6-diol (8.5 g) and triethylamine (11.7 g) were dissolved therein. (Meth)acryloyl chloride (5.6 g) was slowly added, and the resultant mixture was reacted at −10 EC for 6 hours. The reaction mixture was filtered, and evaporated under reduced pressure. The residue was purified by column chromatography to give 9.9 g (yield: 79%) of 2-ethoxyethyloxycarbonyl-5-hydroxy-6-norbornyl(meth)acrylate.

EXAMPLE I

Synthesis of poly[2-tert-butoxycarbonyl-5-hydroxy-6-norbornyl(meth)acrylate/2-carboxylic-5-hydroxy-6-norbornyl(meth)acrylate] copolymer resin (Formula III)

In tetrahydrofuran or toluene (25 g), 2-tert-butoxycarbonyl-5-hydroxy-6-norbornyl(meth)acrylate (0.05 mol) and 2-carboxylic-5-hydroxy-6-norbornyl(meth)acrylate (0.05 mol) were dissolved. Then, 2,2'-azobisisobutyronitrile (AIBN) (0.05 g), as a polymerization initiator, was added thereto, and the reaction was performed at 70 EC under nitrogen or argon atmosphere for 4–24 hours. Crude product thus obtained was precipitated from ethyl ether or hexane, and the precipitate was dried to give 23.2 g (yield: 89%) of the title copolymer resin (Formula III) having molecular weight of 4,000–100,000. The copolymer resin thus prepared, as a chemically amplifiable resist having increased adhesiveness and sensitivity of photoresist, has high glass transition temperature required in the course of the process, and rare absorption in far ultraviolet region, in particular, at 193 Fm. The protective group can be easily removed from the copolymer resin, and the resin is able to form a 0.15 Fm pattern in practical patterning experiment.

EXAMPLE II

Synthesis of poly[2-tert-butoxycarbonyl-5-hydroxy-6-norbornyl(meth)acrylate/2-hydroxyethyl(meth)acrylate/(meth)acrylic acid] copolymer resin (Formula IV)

In tetrahydrofuran or toluene (25 g) 2-tert-butoxycarbonyl-5-hydroxy-6-norbornyl(meth)acrylate (0.05 mol), 2-hydroxyethyl(meth)acrylate (0.04 mol) and (meth)acrylic acid (0.01 mol) were dissolved. Then, 2,2'-azobisisobutyronitrile (AIBN) (0.04 g), as a polymerization initiator, was added thereto, and the reaction was performed at a temperature between 65 EC and 70 EC under nitrogen or argon atmosphere for 4–24 hours. Crude product thus obtained was precipitated from ethyl ether or hexane, and the precipitate was dried to give 21 g (yield: 83%) of the title copolymer resin (Formula IV) having molecular weight of 4,000–100,000. The copolymer resin thus prepared has similar properties to the copolymer obtained in Example I, and the resin is able to form a 0.14 Fm pattern in practical patterning experiment.

EXAMPLE III

Synthesis of poly[2-hydropyranyloxycarbonyl-5-hydroxy-6-norbornyl(meth)acrylate/2-hydroxyethyl(meth)acrylate/(meth)acrylic acid] copolymer resin (Formula V)

In tetrahydrofuran or toluene (20 g), 2-hydroxypyranyloxycarbonyl-5-hydroxy-6-norbornyl(meth)acrylate (0.07 mol), 2-hydroxyethyl(meth)acrylate (0.02 mol) and (meth)acrylic acid (0.01 mol) were dissolved. Then, 2,2'-azobisisobutyronitrile (AIBN) (0.04 g), as a polymerization initiator, was added thereto, and the reaction was performed at a temperature between 65 EC and 70 EC under nitrogen or argon atmosphere for 4–24 hours. Crude product thus obtained was precipitated from ethyl ether or hexane, and the precipitate was dried to give 26 g (yield: 81%) of the title copolymer resin (Formula V) having molecular weight of 4,000–100,000.

The copolymer resin thus prepared, in which the protective group the resin prepared in Example 2 was changed by acetal group, is an excellent copolymer resin having increased sensitivity without deteriorating etching resistance (sensitivity: 100 mJ/cm²).

EXAMPLE IV

Synthesis of poly[2-hydrofuranyloxycarbonyl -5-hydroxy-6-norbornyl(meth)acrylate/2-hydroxyethyl (meth)acrylate/(meth)acrylic acid] copolymer resin (Formula VI)

In tetrahydrofuran or toluene (20 g), 2-hydrofuranyloxycarbonyl-5-hydroxy-6-norbornyl(meth)acrylate (0.07 mol), 2-hydroxyethyl(meth)acrylate (0.02 mol) and (meth)acrylic acid (0.01 mol) were dissolved. Then, 2,2'-azobisisobutyronitrile (AIBN) (0.04 g), as a polymerization initiator, was added thereto, and the reaction was performed at a temperature between 65 EC and 70 EC under nitrogen or argon atmosphere for 4–24 hours. Crude product thus obtained was precipitated from ethyl ether or hexane, and the precipitate was dried to give 25 g (yield: 80%) of the title copolymer resin (Formula VI) having molecular weight of 4,000–100,000. The copolymer resin thus prepared has similar properties to the copolymer obtained in Example III.

EXAMPLE V

Synthesis of poly[2-ethoxyethyloxycarbonyl-5-hydroxy-6-norbornyl(meth)acrylate/2-hydroxyethyl (meth)acrylate/(meth)acrylic acid] copolymer resin (Formula VII)

In tetrahydrofuran or toluene (20 g), 2-ethoxyethyloxycarbonyl-5-hydroxy-6-norbornyl(meth)acrylate (0.07 mol), 2-hydroxyethyl(meth)acrylate (0.02 mol) and (meth)acrylic acid (0.01 mol) were dissolved. Then, 2,2'-azobisisobutyronitrile (AIBN) (0.04 g), as a polymerization initiator, was added thereto, and the reaction was performed at a temperature between 65 EC and 70 EC under nitrogen or argon atmosphere for 4–24 hours. Crude product thus obtained was precipitated from ethyl ether or hexane, and the precipitate was dried to give 20 g (yield: 81%) of the title copolymer resin (Formula VII) having molecular weight of 4,000–100,000. The copolymer resin thus prepared has similar properties to the copolymer obtained in Example III, but it is more excellent in view of contrast.

EXAMPLE VI

One of the copolymer resin (Formula III to VII) (10 g) obtained in Example 1 to 5 was dissolved in 3-methoxymethyl propionate (40 g, solvent), and sulfonium triplate or dibutylnaphthylsulfonium triplate (about 0.2–1 g) as an inorganic acid generator, was added thereto. After stirring, the mixture was filtered to give a photoresist solution. Then the photoresist solution was spin-coated on a surface of a wafer to prepare thin film, and the wafer was preheated in an oven of 70–150 EC or on a hot plate for 1–5 minutes. After exposing to light of 250 nm wavelength by using an exposer, it was post-heated at 90–160 EC. Then, the exposed wafer was impregnated in an aqueous TMAH solution having a concentration of 0.01–5% by weight as a developing solution, for 1.5 minutes to obtain ultra-micro photoresist pattern (resolution: 0.15 Fm).

The copolymer resin according to the present invention is easily prepared by conventional radical polymerization due to the introduction of norbornyl(meth)acrylate unit to a structure of copolymer for photoresist. The resin has high transparency at 193 nm wavelength, provides increased etching resistance and enhanced adhesive strength due to a hydrophilic functional group in the norbornyl group, and shows excellent resolution of 0.15 Fm.

Many modifications and variations of the present invention are possible in light of the above teachings. Therefore, it is to be understood that within the scope of the appended claims, the invention may be practiced otherwise than as specifically described.

What is claimed is:

1. A monomer comprising:
   5-hydroxy-6-norbornyl(meth)acrylate derivative represented by Formula II:

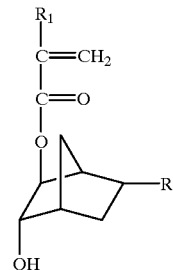

wherein R is selected from the group consisting of 2-tert-butoxycarbonyl, 2-carboxylic, 2-hydropyranyloxycarbonyl, 2-hydrofuranyloxycarbonyl and 2-ethoxyethyloxycarbonyl and $R_1$ is hydrogen or methyl.

2. The monomer of claim 1 selected from the group consisting of 2-tert-butoxycarbonyl-5-hydroxy-6-norbornyl (meth)acrylate, 2-carboxylic-5-hydroxy-6-norbornyl(meth) acrylate, 2-hydropyranyloxycarbonyl-5-hydroxy-6-norbornyl(meth)acrylate, 2-hydroxyfuranyloxycarbonyl-5-hydroxy-6-norbornyl(meth)acrylate and 2-ethoxyethyloxycarbonyl-5-hydroxy-6-norbornyl(meth) acrylate.

3. A process for preparing a monomer comprising:
   synthesizing 2-tert-butoxycarbonyl-5-norbornene by reacting cyclopentadiene with tert-butyl acrylate;
   chilling the 2-tert-butoxycarbonyl-5-norbornene in acetone;
   reacting the 2tert-butoxycarbonyl-5norbornene in acetone with potassium permanganate in an aqueous alkaline solution to prepare 2-tert-butoxycarbonylnorbornan-5,6-diol;
   dissolving the 2-tert-butoxycarbonylnorbornan-5,6-diol with triethyl amine in tetrahydrofuran; and
   reacting the solution with (meth)acryloyl chloride to synthesize 2-tert-butoxycarbonyl-5-hydroxy-6-norbornyl(meth)acrylate.

4. The process of claim 3 wherein the chilling step is maintained at a temperature ranging from about −40° C. to about −60° C.

5. A process for preparing a monomer comprising:
   synthesizing 2-tert-butoxycarbonyl-5-norbornene by reacting cyclopentadiene with tert-butyl acrylate;
   reacting the 2-tert-butoxycarbonyl-5-norbornene with an oxidant in a solvent to obtain 2-tert-butoxycarbonylnorbornan-5,6-diol; and
   dissolving the 2-tert-butoxycarbonylnorbornan-5,6-diol, triethylamine and (meth)acryloyl chloride in a solvent and reacting the 2-tert-butoxycarbonylnorbornan-5,6- diol with the triethyl amine and (meth)acryloyl chloride to synthesize 2-tert-butoxycarbonyl-5-6-norbornyl (meth)acrylate.

6. The process of claim 5 wherein the oxidant is potassium permanganate.

7. A process for preparing a monomer comprising:

reacting cyclopentadiene with acrylic acid to synthesize 5-norbornene carboxylic acid;

reacting the obtained 5-norbornene carboxylic acid with an oxidant in a solvent to obtain 5-norbornencarboxylic-5,6-diol; and reacting the 5-norbornencarboxylic-5,6-diol with triethylamine and (meth)acryloyl chloride in a solvent to synthesize 2-carboxylic-5-hydroxy-6-norbornyl(meth) acrylate.

8. The process of claim 7 wherein the oxidant is potassium permanganate.

9. A process for preparing a monomer comprising:

reacting cyclopentadiene with hydropyranyl acrylate to synthesize 2-hydropyranyloxycarbonyl-5-norbornene;

reacting the 2-hydropyranyloxycarbonyl with an oxidant in a solvent to obtain 2-hydropyranyloxycarbonylnorbornan-5,6-diol; and reacting the 2-hydropyranyloxcarbonylnorbornan-5,6-diol with triethylamine and (meth)acryloyl chloride in a solvent to synthesize 2-hydropyranyloxycarbonyl-5-hydroxy-6-norbornyl(meth)acrylate.

10. The process of claim 9 wherein the oxidant is potassium permanganate.

11. A process for preparing a monomer comprising:

reacting cyclopentadiene with hydrofuranyl acrylate to synthesize 2-hydrofuranyloxycarbonyl-5-norbornene;

reacting the 2-hydrofuranyloxycarbony-5-norborene with an oxidant in a solvent to obtain 2-hydrofuranyloxycarbonylnorbornan-5,6-diol; and reacting the 2-hydrofuranyloxycarbonylnorbornan-5,6-diol with triethylamine and (meth)acryloyl chloride in a solvent to synthesize 2-hydrofuranyloxycarbonyl-5-hydroxy-6-norbornyl(meth)acrylate.

12. The process of claim 11 wherein the oxidant is potassium permanganate.

13. A process for preparing a monomer comprising:

reacting cyclopentadiene with ethoxyethyl acrylate to synthesize 2-ethoxyethyloxycarbonyl-5-norbornene;

reacting the 2-ethoxyethyloxycarbonyl-5-norbornene with an oxidant in a solvent to obtain 2-ethoxyethyloxycarbonylnorbornan-5,6-diol; and reacting the 2-ethoxyethyloxycarbonylnorbornan-5,6-diol with triethylamine and (meth)acryloyl chloride in a solvent to synthesize 2-ethoxyethyloxycarbonyl-5-hydroxy-6-norbornyl(meth)acrylate.

14. The process of claim 13 wherein the oxidant is potassium permanganate.

* * * * *

UNITED STATES PATENT AND TRADEMARK OFFICE
CERTIFICATE OF CORRECTION

PATENT NO.    : 6,372,935 B1
DATED         : April 16, 2002
INVENTOR(S)   : Jung et al.

It is certified that error appears in the above-identified patent and that said Letters Patent is hereby corrected as shown below:

Column 14,
Line 46, please insert -- - -- (hyphens) after "2" and "5".

Signed and Sealed this

Eighteenth Day of February, 2003

JAMES E. ROGAN
*Director of the United States Patent and Trademark Office*